(12) United States Patent
Tibbits et al.

(10) Patent No.: US 10,195,294 B2
(45) Date of Patent: Feb. 5, 2019

(54) PROGRAMMABLE BACTERIAL TATTOO

(71) Applicant: BIOINK CORPORATION, San Francisco, CA (US)

(72) Inventors: Skylar J E Tibbits, Boston, MA (US); Marcelo Coelho, Boston, MA (US); Tal Danino, New York, NY (US); Carlos Olguin, San Francisco, CA (US)

(73) Assignee: LOGICINK CORPORATION, San Francisco, CA (US)

(*) Notice: Subject to any disclaimer, the term of this patent is extended or adjusted under 35 U.S.C. 154(b) by 0 days.

(21) Appl. No.: 15/162,438

(22) Filed: May 23, 2016

(65) Prior Publication Data

US 2016/0339120 A1 Nov. 24, 2016

Related U.S. Application Data

(60) Provisional application No. 62/165,493, filed on May 22, 2015.

(51) Int. Cl.
| | | |
|---|---|---|
| *C12Q 1/02* | (2006.01) | |
| *A61K 49/00* | (2006.01) | |
| *A61K 8/99* | (2017.01) | |
| *A61K 8/02* | (2006.01) | |
| *A61Q 1/02* | (2006.01) | |

(52) U.S. Cl.
CPC ........ *A61K 49/0006* (2013.01); *A61K 8/0208* (2013.01); *A61K 8/99* (2013.01); *A61Q 1/025* (2013.01); *C12Q 1/025* (2013.01); *A61K 2800/74* (2013.01)

(58) Field of Classification Search
None
See application file for complete search history.

(56) References Cited

U.S. PATENT DOCUMENTS

| | | | |
|---|---|---|---|
| 4,382,063 A | 5/1983 | Romito et al. | |
| 4,788,432 A | 11/1988 | Patel | |
| 5,899,856 A | 5/1999 | Schoendorfer et al. | |
| 6,251,083 B1 | 6/2001 | Yum et al. | |
| 6,706,099 B2 | 3/2004 | Sir et al. | |
| 7,969,307 B2 | 6/2011 | Peeters | |
| 2007/0160814 A1 | 7/2007 | Mercolino | |
| 2008/0107699 A1* | 5/2008 | Spigelman | A01N 63/00 424/404 |
| 2009/0325221 A1* | 12/2009 | Long | A61B 5/14539 435/34 |
| 2011/0106000 A1* | 5/2011 | Jones | A23B 4/16 604/23 |
| 2015/0126834 A1 | 5/2015 | Wang et al. | |
| 2017/0071536 A1 | 3/2017 | Tibbits | |
| 2017/0325737 A1 | 11/2017 | Alvarez | |

FOREIGN PATENT DOCUMENTS

| | | |
|---|---|---|
| WO | WO 2016/090189 | 6/2016 |
| WO | WO 2018/144627 | 8/2018 |

OTHER PUBLICATIONS

Jia et al. 2013 (Electrochemical Tattoo Biosensors for Real-Time Noninvasive Lactate Monitoring in Human Perspiration; Analytical Chemistry 85:6553-6560).*
Lei et al. 2006 (Microbial Biosensors; Analytica Chimica Acta 568: 200-210).*
Lei et al. 2006 (Microbial biosensors; Anaytica Chimica Acta 568: 200-210).*
Martinez et al. 2008 (Three-dimensional microfluidic devices fabricated in layered paper and tape; PNAS 105(50): 19606-19611).*
Bjerketorp et al. 2006 (Advances in preservation methods: keeping biosensor microorganisms alive and active; Current Opinion in Biotechnology 17:43-49).*
MacNab et al. 1972 (The Gradient-Sensing Mechanism in Bacterial Chemotaxis; Proc. Nat. Acad. Sci. 69(9): 2509-2512).*
Bartolo et al. 2007 (Microfluidic Stickers; Lab on a Chip 8:274-279) (Year: 2007).*
Rothert et al. 2005 (Whole-cell-reporter-gene-based biosensing systems on a compact disk microfluidics platform; Analytical Biochemistry 342: 11-19) (Year: 2005).*
Danino et al., "A synchronized quorum of genetic clocks," Nature, 2010, pp. 326-330, plus 9 pgs. of Supplementary Information, vol. 463.
Prindle et al., "A sensing array of radically coupled genetic 'biopixels'," Nature, 2012, pp. 39-44, vol. 481.
Su et al., "Microbial biosensors: A review", Biosensors and Bioelectronics, 2011, pp. 1788-1799, vol. 26.
U.S. Appl. No. 15/451,065, Carlos Edel Olguin Alvarez, Communication Using Programmable Materials, filed Mar. 6, 2017.
U.S. Appl. No. 15/358,415 Office Action dated Sep. 19, 2017.
PCT/US18/16281, Cumulative Biosensor System to Detect Alcohol, Jan. 31, 2018.
U.S. Appl. No. 15/358,415, Final Office Action dated Apr. 9, 2018.
PCT Application No. PCT/US2018/016281 International Search Report and Written Opinion dated May 29, 2018.
U.S. Appl. No. 15/358,415 Office Action dated Nov. 2, 2018.

* cited by examiner

*Primary Examiner* — Mary Maille Lyons
(74) *Attorney, Agent, or Firm* — Polsinelli LLP

(57) ABSTRACT

This disclosure relates to a tattoo decal containing bacteria that can be applied to skin and function as both a monitoring sensor and a visual indicator. In particular, a temporary tattoo containing a bacteria composite that may be selected or "programmed" to sense, detect, or otherwise react to a variety of stimuli for use in a variety of applications and industries is disclosed.

20 Claims, 9 Drawing Sheets

PROGRAMMABLE BACTERIAL TATTOO

CROSS-REFERENCE TO RELATED APPLICATIONS

The present application claims the priority benefit of U.S. provisional application No. 62/165,493 filed May 22, 2015 and entitled "Programmable Bacterial Tattoo," the disclosure of which is incorporated herein by reference in its entirety.

BACKGROUND OF THE INVENTION

Field of the Disclosure

This disclosure relates generally to bacterial-based diagnostic devices. In particular, the disclosure relates to a tattoo decal containing bacteria that can be applied to skin and function as both a monitoring biosensor and a visual indicator.

Description of the Related Art

Presently available tattoos, traditional temporary tattoos, stickers, and other adhesive graphic patterns are generally static. Additionally, they typically lack the ability to transform or change in response to stimuli or other conditions. As such, they are unable to convey information that changes or varies with time. These devices are therefore ill-suited for use as biosensors. Additionally, existing wearable sensors or devices tend to be bulky electronic products that add weight and volume, thereby resulting in discomfort and aesthetic concerns. These devices are also fundamentally power-constrained and may rely on battery packs, solar power, or other power sources. Other existing devices often require external power, which in turn adds weight, bulk, and safety concerns.

SUMMARY OF THE CLAIMED INVENTION

The present disclosure generally relates to a biosensor tattoo, particularly a bacterial-based tattoo that includes a bacterial composite that generates a response when exposed to an analyte. As used herein, tattoo refers to a decal (e.g., in a design) that may be applied and adhere to a surface. In one embodiment, the bacterial tattoo includes a bacterial composite deposited on an adhesive substrate. In one aspect, the adhesive substrate further includes a porous membrane to permit substances to traverse across the substrate in a desired direction. In another aspect, the adhesive substrate may be porous itself. Other embodiments of the tattoo include additional layers for the application, sterility, or protection of the tattoo. These layers may include a removable backer, a water-soluble layer, and an encapsulation layer.

According to other embodiments, the bacterial composite includes one or more bacterial strains selected or modified to respond to particular substances in a particular manner. The bacterial strains may be encapsulated and/or suspended to provide a bacterial-based ink in a customizable temporary tattoo design.

In various embodiments, the bacterial tattoo provides a visual display or otherwise detectable response upon exposure to an analyte of interest. In one aspect, the visual display may provide for the generation or transformation of text, an image, graphic, or other indicia. In various embodiments, the text, image, graphic or other indicia may be predetermined or generated randomly to allow the tattoo to function as aesthetic or ornamental display device.

DETAILED DESCRIPTION

Figure 1A:
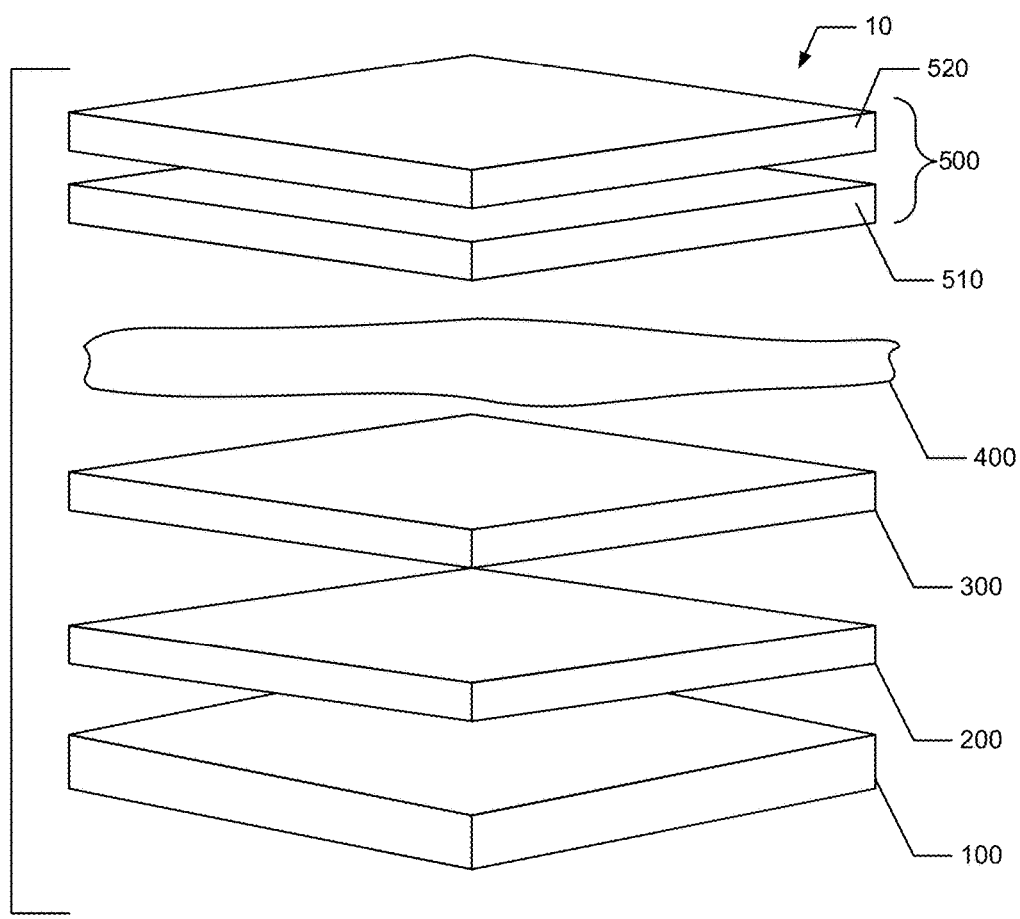
FIG. 1A is perspective view of the various layers for a programmable bacterial tattoo according to one embodiment.

Various embodiments of the programmable tattoo disclosed herein relate to a removable or temporary tattoo device that is applied to any surface of a person, animal, or any object. In one aspect, the tattoo device allows a user to apply the bacteria-based sensor directly to the skin of a person easily without direct contact between the skin and the bacteria contained within the tattoo. In another aspect, the tattoo device is removable and can be customized to include a variety of visual designs, sensor designs, and sensor functionality. In yet another aspect, the tattoo device may be applied to other objects and surfaces, including but not limited to products, packaging, clothing, machinery, and vehicles.

In other embodiments, the bacterial tattoo of the present disclosure would allow the creation and/or manipulation of custom graphics whose appearance may be based on the current internal environment, external environment, passage of time, or combinations thereof. Thus, such tattoo may serve as a fluid interface to convey real-time information. Similarly, the devices disclosed herein could be used to customize the visual appearance of existing tattoo or graphics, rather than being constrained to a single static design. This provides numerous possibilities for transforming skin ornamentation, apparel, packaging, and artwork visually and/or physically. As a result, the tattoos disclosed herein may present fluid images similar to that of a digital display device.

In one embodiment, a programmable bacterial tattoo is composed of multiple layers of various materials, each possessing different functional properties within the bacterial tattoo. In one aspect, the various functions performed by one or more of the various layers include adhering to and immobilizing the bacterial composite, while providing pathways for the substances or other environmental conditions to be detected or monitored to reach the bacteria. Additionally, one or more layers of the tattoo provide adhesion to the application site (e.g. a user's skin or other surface of the target being monitored). In various other aspects, the layers can be laminated together through any suitable technique, including but not limited to gluing, heat bonding, chemical bonding, mechanical adhesion, or combinations thereof. etc.

In contrast to traditional biosensors, whole-cell bacteria biosensors have several advantages. Their large population size, rapid growth rate, low cost, and easy maintenance make them a lucrative option for environmental monitoring. Further, an additional advantageous characteristic of bacteria is that they can be "tailored" or "programmed" to respond by a detectable signal to pre-specified changes in their environmental conditions. Alternatively, biomolecules or responsive chemicals may serve as the bases for biosensing ink.

Bacterial tattoos do not require traditional forms of power and are not constrained by the same power safety concerns as wearable electronics. By utilizing bacteria as a natural programmable sensing technology, this invention can become far more scalable to sense, compute and display a variety of dynamic patterns and information without traditional requirements of electronics and power.

The Programmable Bacterial Tattoo Device

FIG. 1A is a perspective view of one embodiment of the programmable bacterial tattoo 10. As shown, the bacterial tattoo 10 includes a plurality of layers. In the embodiment shown, the tattoo includes a removable backer 100, a water-soluble layer 200 for removing the backer, a cover or encapsulation layer 300, a bacteria-composite layer 400, and an adhesive substrate layer 500. In various embodiments, the removable backer 100 provides a rigid structure to the tattoo 10 for shipping and/or handling before application of the tattoo. The removable backer may be paper, cardstock, a polymer, or other suitable surface for displaying printed information, such as instructions or other indicia for the tattoo. The backing paper 100 may be any material commonly used as a backing paper for aesthetic or ornamental temporary tattoos. Similarly, to aesthetic or ornamental temporary tattoo, the backer 100 is removed during application by the dissolution of the water-soluble layer 200. The water-soluble layer 200 may include silicone or any material commonly used to engage the backing paper for aesthetic or ornamental temporary tattoos. Similar to ornamental temporary tattoos, the water-soluble layer 200 dissolves when the tattoo or surface where the tattoo is to be applied is wetted thereby releasing the encapsulation layer 300 for transfer to the application site 20.

Figure 1B:
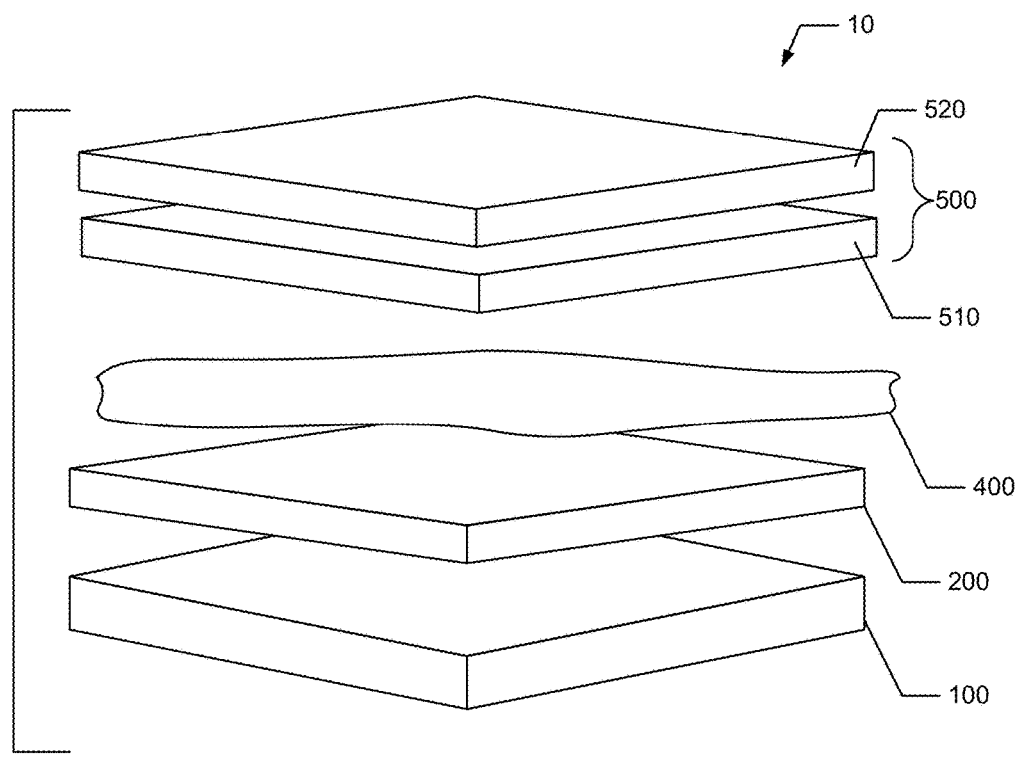
FIG. 1B is perspective view of the various layers for a programmable bacterial tattoo according to one embodiment.
Figure 3:
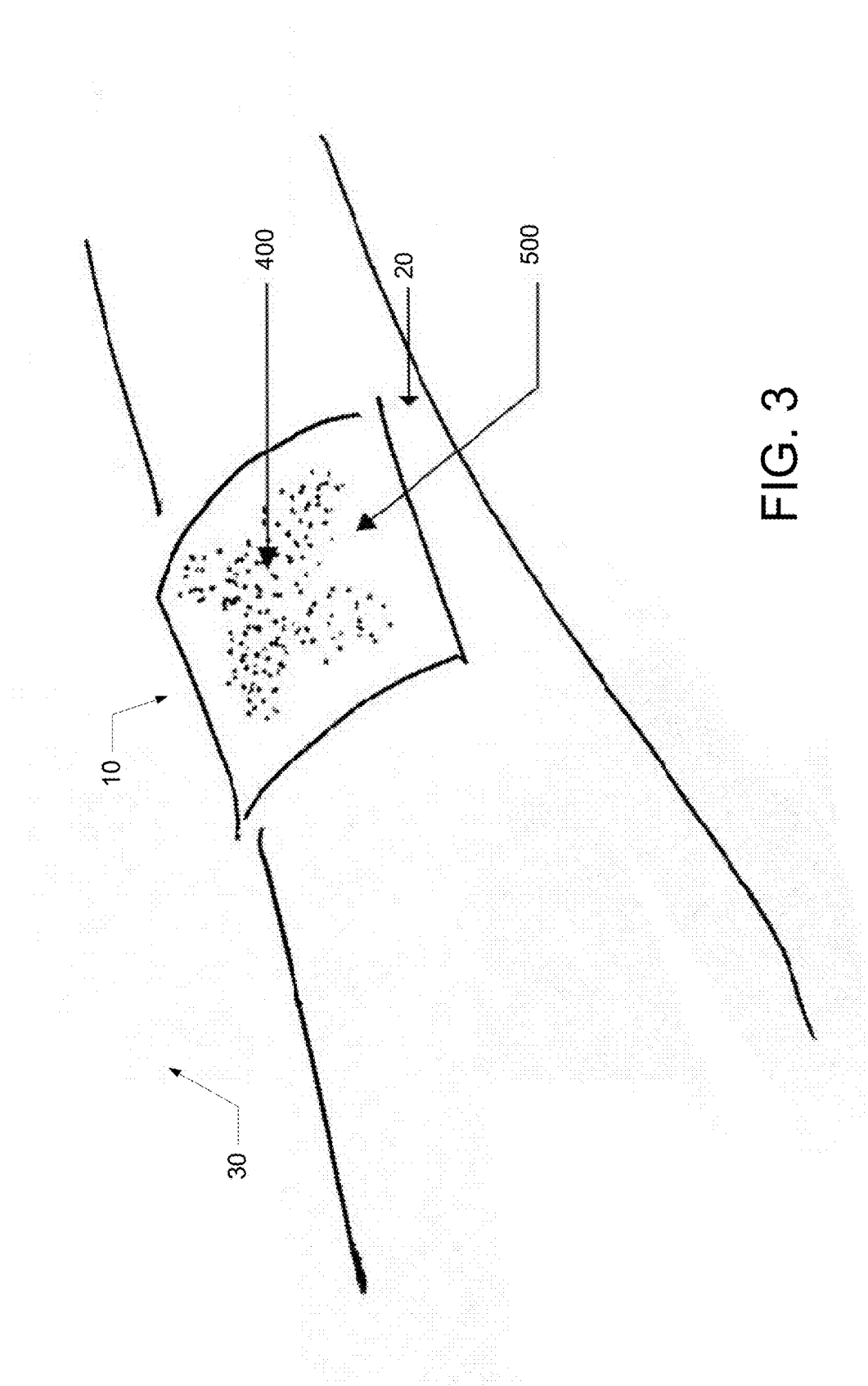
FIG. 3 is an illustration of one embodiment of the programmable bacterial tattoo attached to a wearer's skin.
Figure 4:
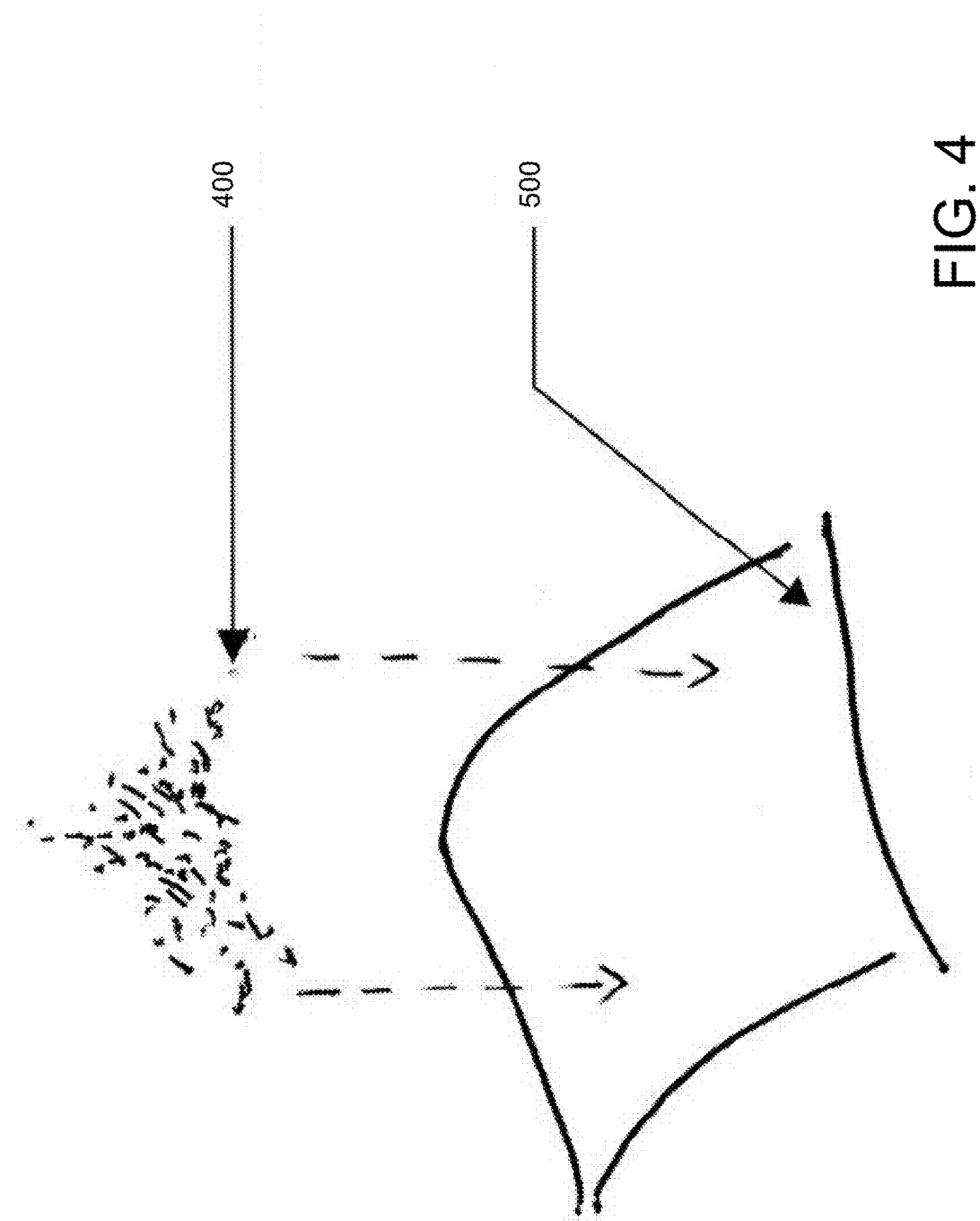
FIG. 4 is an illustration of a bacterial composite deposited onto a substrate according to one embodiment of the programmable bacterial tattoo.
Figure 5:
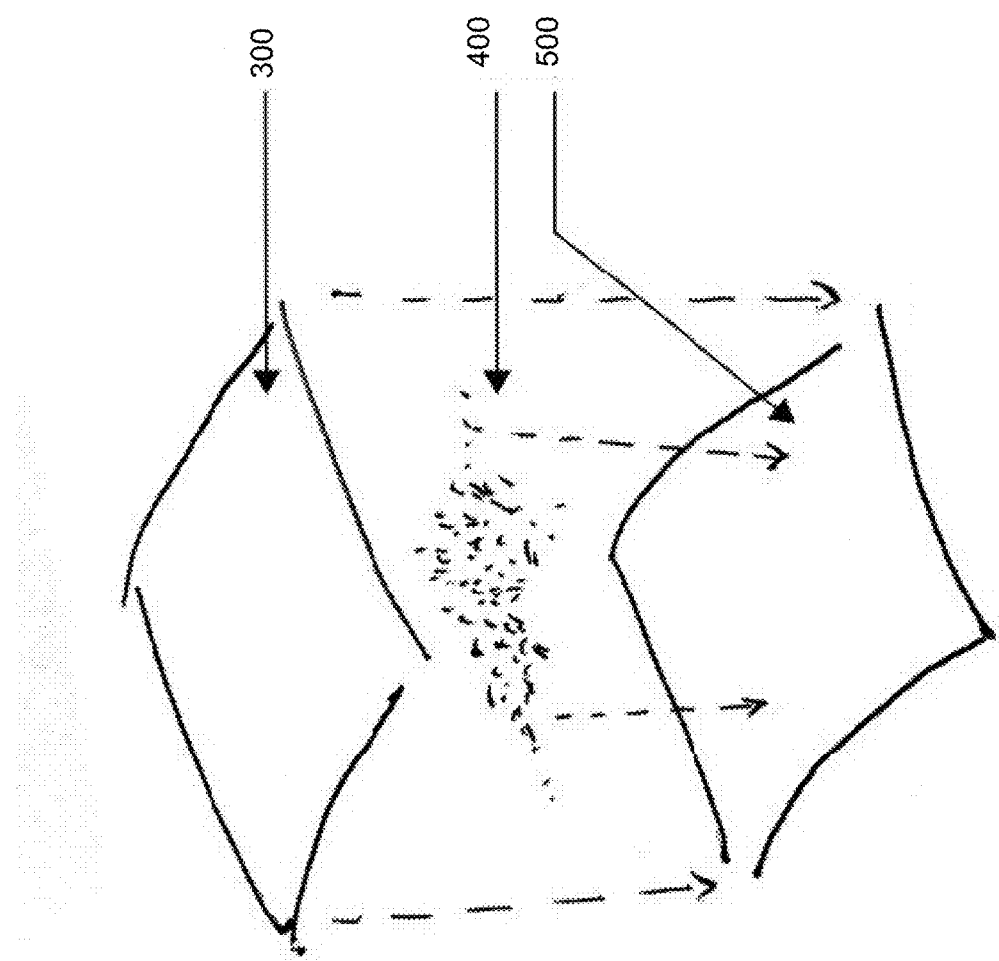
FIG. 5 is an illustration of a bacterial composite deposited between an encapsulation layer and a substrate according to one embodiment of the programmable bacterial tattoo.
Figure 8:
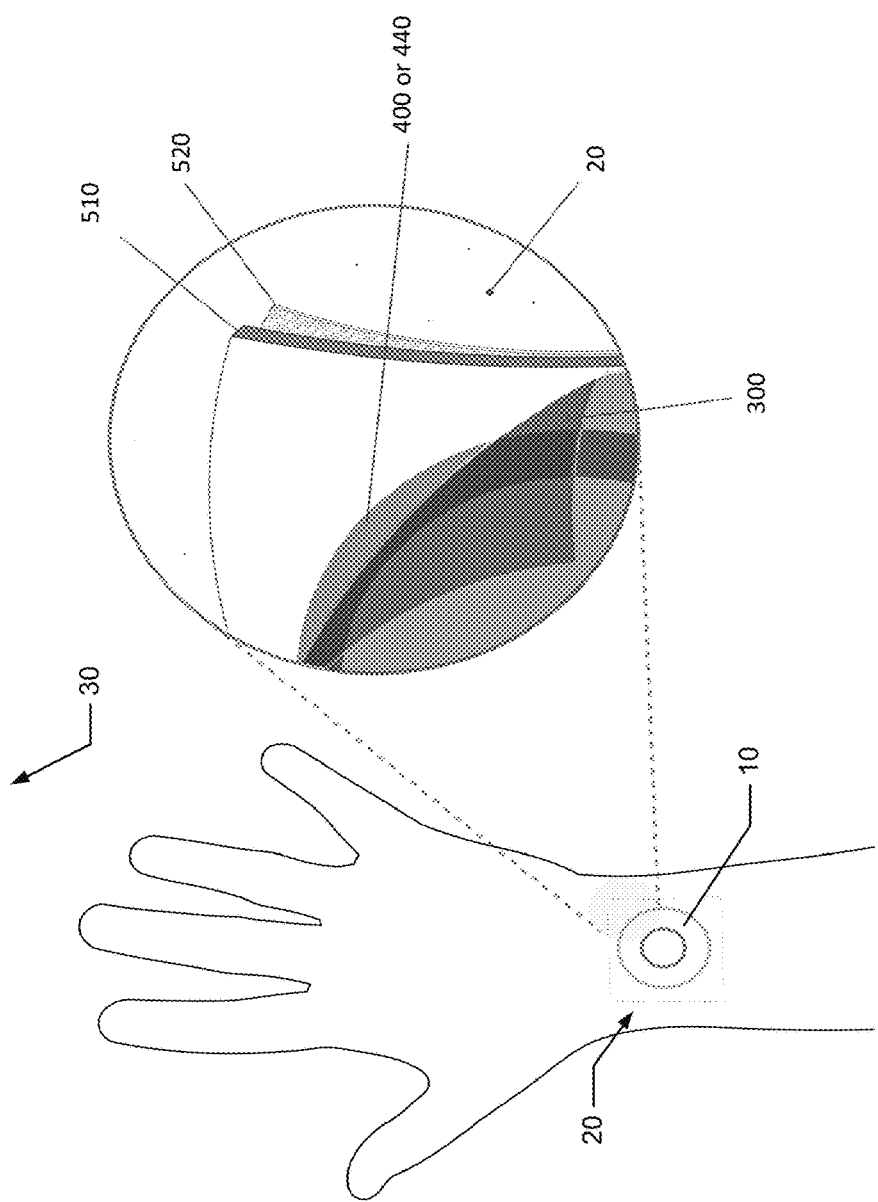
FIG. 8 is an illustration of one embodiment of the programmable bacterial tattoo attached to a wearer's skin.

The encapsulation layer 300 protects the bacteria composite 400 from the external environment 30, as shown in FIGS. 3 and 8. When applied to a person, animal, or object, the encapsulation layer 300 also protects the user from contacting the bacterial composite 400 directly whether intentionally or accidentally. In various embodiments, the encapsulation layer 300 incorporates a porous membrane which may be selected to permit one or more substances to traverse the layer and contact the bacterial composite 400. Alternatively, the encapsulation layer 300 may act as hermetic barrier to the bacterial composite 400. As shown in FIG. 1B, the encapsulation layer may be omitted entirely, in certain embodiments.

Figure 2:
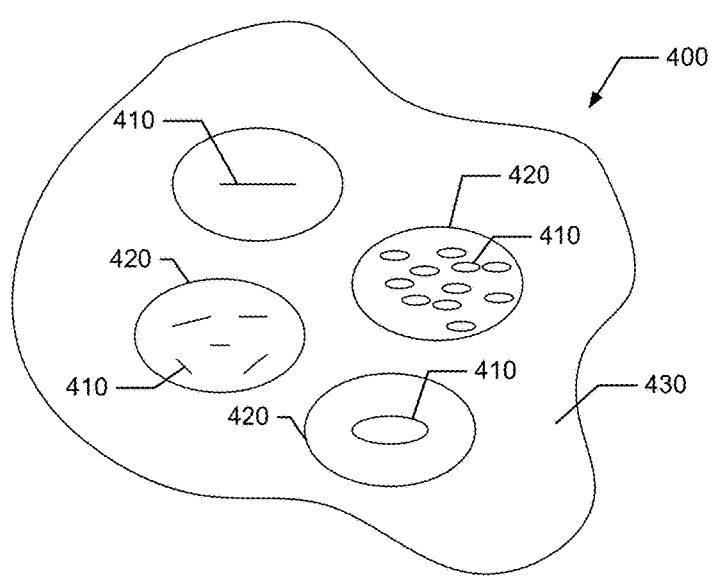
FIG. 2 is an illustration of microencapsulated bacteria within the programmable bacterial tattoo according to one embodiment

As explained more fully below, the bacteria composite 400 is a liquid or gelatinous composition containing one or more bacterial strains. As shown in FIG. 2, the bacteria 410 are further encapsulated in microcapsules 420. The bacteria composite 400 may be deposited or printed in any design (e.g. alphanumeric text, graphics, or other indicia). In various embodiments, the bacterial composite 400 may be printed using a piezoelectric inkjet printer. In other embodiments, the composite 400 may be printed using other printing techniques, including but not limited to deposition, silk-screening, lithography, or combinations thereof. Additionally, the bacteria within the bacteria composite may be selected or "programmed" to sense, detect, or otherwise react to a variety of stimuli. As such, the bacterial tattoo 10 can be configured for use in a variety of applications and industries.

The adhesive substrate layer 500 is engaged to the bacteria composite 400 opposite the encapsulation layer 300 and is designed to removably adhere to an application site for a period of time. As shown in FIGS. 1A and 1B, the adhesive substrate layer 500 may further be formed from a reaction layer 510 upon which the bacteria composite 400 is printed or otherwise deposited. The adhesive substrate may also include a one-way porous membrane 520 that is disposed between the reaction layer and an application site. The one-way membrane 520 permits substances to traverse the through the membrane towards the reaction layer, while preventing migration of substances out of the reaction layer towards the application site. The one-way membrane 520 is preferably used when the tattoo 10 is applied to a person. In other embodiments, the one-way membrane 520 is omitted from the tattoo 10, when it is desirous to permit substances to freely traverse into and out of the bacteria composite. In conjunction with the various other layers 100, 200, or 300, adhesive substrate layer 500 essentially creates a pocket to both house and retains the bacteria composite 400 within the tattoo 10.

In various embodiments, the tattoo 10 is configured to sense, detect, or otherwise react to internal stimuli or stimuli external to the user or object to which the tattoo is applied. As used herein, internal stimuli refers to a stimulus originating from or emanating from the user or object being monitored. These include, but are not limited to molecules, chemical compounds, heat, light, radiation and combinations thereof. External stimuli refers to environmental stimuli that may affect the person or object being monitored. An analyte sensed, detected, monitored, and/or measured by the tattoo 10 may include internal stimuli, external stimuli, or both. As such, one or more of the layers 100-300 and 500 may be modified or configured to selectively permit the passage of stimuli to the bacterial composite 400. By way of example and not limitation, the layers of the tattoo may be configured such that they are absorbent to only particular chemicals or particle sizes, while blocking the passage of other chemicals, particles or bacteria.

In other embodiments, the tattoo 10 may be configured to sense, monitor, or detect stimuli as a function of time. For example, the bacterial composition 400 may be configured to function with time-release capabilities where the quantity of the bacterial composite that can react with the stimuli is made available over time. This may be accomplished using time-release or sustained-release technology commonly used with pharmaceuticals. Alternatively, the tattoo 10 may be configured such that the bacterial composition 400 produces a response after the passage of time, whether based on or regardless of stimuli.

The layers of the tattoo 10 may be composed of or at least include gels or porous membranes. Additionally, the layers may include a sealant to prevent the accumulation of undesired moisture. Similarly, sealants may be used to prevent evaporation in the bacteria composite layer. In various embodiments, the sealant may be added to an interior surface (facing the application), an external site (facing away from the application site), or both.

As shown in FIGS. 3 and 8, the tattoo 10 can be directly applied to a person's skin to provide a wearable "smart tattoo." Alternatively, the tattoo 10 can be applied to clothing, or other objects to provide a removable sensor. Depending on the configuration and selection of the bacteria, the resulting display of the tattoo 10 in response to the stimuli may be configured to display any of a variety of visual representations.

When applied the bottom-most layer is the adhesive substrate layer 500 prevents direct contact between the application site and bacteria while, in at least one embodiment, mediating the one-directional flow of particles or chemicals from the application site toward the bacteria composite 400. Although referred to herein as a tattoo, the disclosed bacterial tattoo 10 is not inserted into the dermis layer of skin. Preferably, the bacterial tattoo 10 is provided as a temporary removable device, similar to a sticker or a temporary tattoo. Therefore, in one or more embodiments, the adhesive substrate 500 a pressure or moisture-based adhesive to provide direct, yet temporary adhesion.

Figure 6:
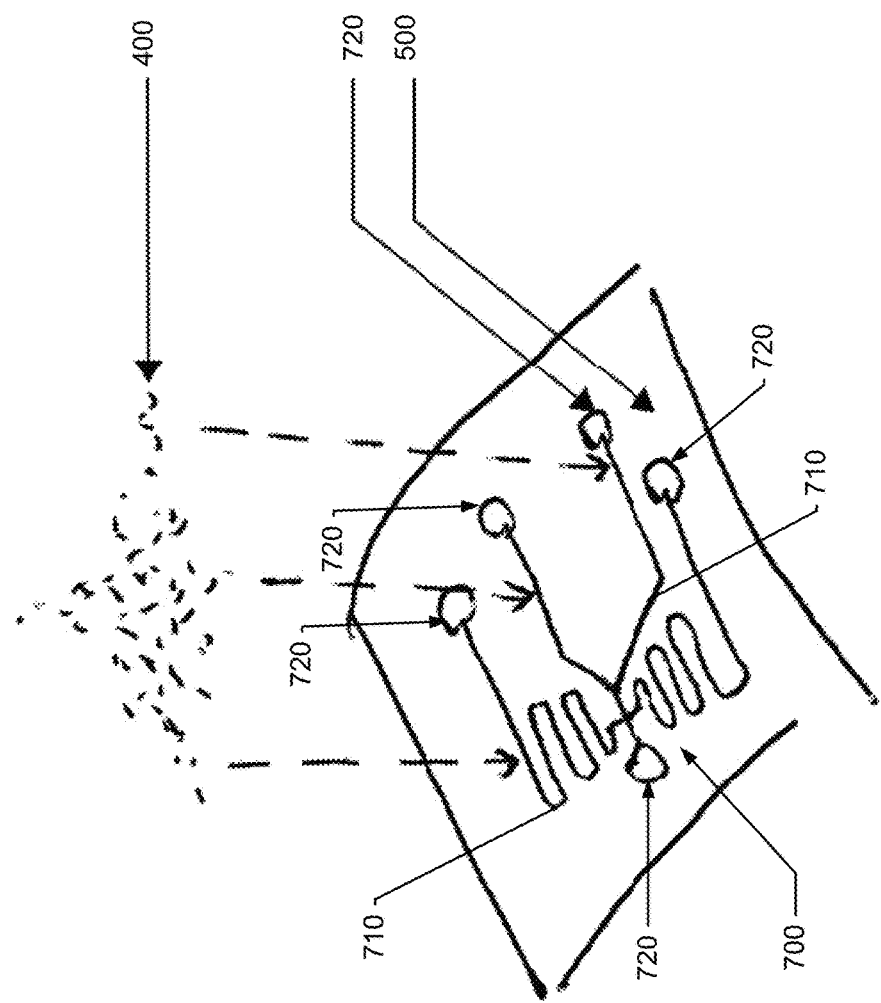
FIG. 6 an illustration of a bacterial composite deposited onto microfluidic channels patterned on a substrate according to one embodiment of the programmable bacterial tattoo.

In one embodiment, as shown in FIG. 6 the substrate later 500 may be patterned with microfluidic channels 700, spotted with different adhesives or textures or other functional patterns that enhance the core functionality of the bacteria. In one embodiment, the response of the bacterial composite 400 would be governed by a logic-based configuration of the microfluidic channels 700 to create "if-then" conditions or pathways 710 for the bacteria to physically move or fill. In another embodiment, the microfluidic channels 700 provide different sites 720 for unique types of bacteria to be housed and separated such that the tattoo may sense and detect a plurality of analytes simultaneously. For example, the microfluidic channels 700 may be divided to contain bacteria that respond to thermal changes, bacterial that respond to a chemical analyte and those that respond to the presence of a metal, allowing the simultaneous monitoring of a variety of parameters. In yet another embodiment, the microfluidic channels 10 may be configured to create patterns which may help enhance the visual display or pattern produced by the bacteria such that the user can more easily visually distinguish indicators. One or more additional layers of patterning may also provide improved functionality for observing visual indications.

The Bacterial Composite

Bacteria are among the most versatile biosensors in the natural world, sensing a vast array of chemical, environmental conditions and responding with genetic programs encoded in their DNA for a particular function. One of the classic examples is that of the lac operon, in which bacteria response to the presence of lactose by removing a repressor of gene expression and producing a cascade of enzymes to transport and enzymatically process more of this sugar. This occurs only after 'sensing' lactose, thereby conserving energy on an otherwise unnecessary enzyme. This also includes molecular logic to decrease production of these enzymes when higher enemy sugars such as glucose are present.

According to various embodiments, the bacterial composite 400 is provided as an ink that includes one or more bacterium disposed inside of microcapsules 420, as shown in FIG. 2. The microcapsules 420 provide an additional barrier between the bacterial and the application site. In one embodiment, the microcapsules 420 are composed of agarose or alginate, which allows the bacterial to sense external molecules via diffusion into the thin gel layer of the microcapsules. The encapsulated bacteria may then be suspended in a fluid medium 430 (e.g., an ink), thereby forming a viscous substance that is engaged to the substrate layer 500. In various embodiments, the bacterial composite 400 is sealed between the substrate layer 500 and the encapsulation layer 300. Alternatively, the bacterial composite 400 may be retained within a microfluidic device 700, engaged to the substrate layer 500, as shown in FIG. 6.

Previous work regarding engineered bacteria has been performed to provide bacteria that to respond to the presence of other bacteria via quorum-sensing molecules, such as described in the article entitled "A synchronized quorum of genetic clock"; T. Danino, et. al; Nature vol. 463, 326-330, 2010 and "Supplemental Information" pages 1-9 at http://www.nature.com/nature/journal/v463/n7279/suppinfo/nature08753.html Additionally, bacteria have been developed that produce dynamic responses to the presence of arsenic in liquid samples, such as described those in the article "A sensing array of radically coupled genetic 'biopixels'", Prindle et al, Nature vol. 481, 39-44 2012). In the latter example, bacteria were engineered as complex sensors to produce fluorescent proteins at different frequencies depending on how much arsenic was present in on microfluidic channels.

Figure 7:
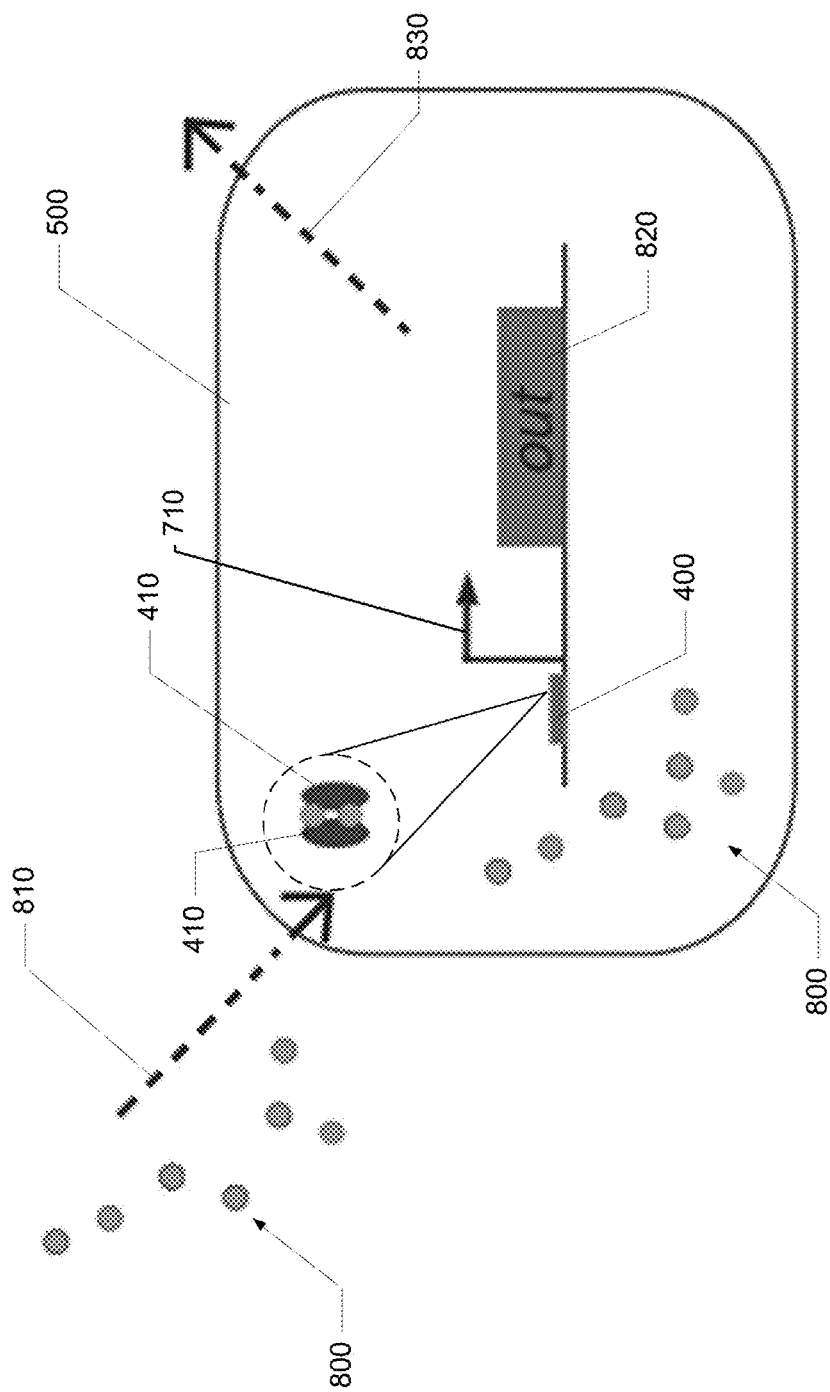
FIG. 7 is a schematic illustration of the programmable bacterial tattoo providing a visual display in response to an analyte according to one embodiment.

Using synthetic biology techniques, the bacteria for use in the bacterial composite 400 may be genetically altered such that analyte response, molecular logic, and signal response mechanisms within the bacteria are manipulated to provide custom biosensors for a wide variety of applications. By way of example, FIG. 7 provides a simplified depiction of a response generated by bacteria 410 within the bacterial composite 400 when exposed to an analyte 800.

According various embodiments of the bacterial tattoo 10, a wide variety of input molecules or analytes may be measured or monitored. Additionally, a wide variety of responses, including but not limited to optical, thermal, and electrical readouts, among others, or combinations thereof may be generated. In one aspect, the response may be manifested by cell death within the composite 400. In other aspects, the response may be manifested by a by-product or metabolite produced within the composite. As disclosed herein, responses may be generated in a number of other ways. These outputs may be observed or otherwise discerned directly from the tattoo 10. Alternatively, in one or more embodiments, the outputs may be measured, quantified, or otherwise determined through one or more external devices (not shown) that interface with the infrastructure of the tattoo 10.

By way of example, the bacterial composite 400 may include bacteria that are selected or "programmed" to sense, detect, monitor, and/or measure the presence of metals, such as nickel, cobalt, mercury, copper, arsenic, iron, cadmium, metal, and genotoxic substances, among others. In various other embodiments, the bacterial composite 400 may be configured to sense, detect, monitor, and/or measure the presence of sugars (e.g. galactose, sucrose, lactose, glucose, among others), ethanol, ultraviolet radiation, infrared radiation, ionizing radiation, changes in temperature, and other microorganisms via quorum sensing.

In various embodiments, the bacterial composite may include, or is at least deposited on the substrate layer 500 with one or more other reagents, enzymes, growth or culture media, or combinations thereof, to aid the analyte uptake, bacterial response, or output from the tattoo 10.

Aside from use with a bacterial composite, the substrate layer 500 may be printed with one or more bio-sensor compound 440 to provide a broad-based biosensor tattoo that does not necessarily rely on a bacterial response to stimuli. For example, the bio-sensor compound may include dried probiotics, cell-free enzymes, responsive chemicals, or combinations thereof.

Example Outputs

According to various embodiments of the bacterial tattoo 10, the readouts or outputs produced in the presence of a desired analyte or other internal or external stimuli include but are not limited to optical output, electrical readouts, variance in motility and visual displays. Optical outputs may be observed by fluorescence, colorimetric changes, luminescence, chemiluminescence, or combinations thereof. Electrical readouts may be observed by changes in pH, changes in conductivity through the bacterial composite, or combinations thereof. Motility variance may be observed by changes in the tumbling, swimming, spreading behavior of the bacteria of the composite 400 or a reagent, or combinations thereof. Other outputs that may be observed include variations in rugosity, smell, temperature, taste, or combinations thereof.

In preferred embodiments, the bacterial tattoo 10 provides a visual display when a desired analyte is present or varies. In particular, there are a number of mechanisms by which a visual or physical display of the bacterial tattoo may indicate the detection of a certain internal/external stimuli. By way of example and not limitation, visual changes may be brought about by changes in the densities or other gradients of bacteria—which may be arranged in the same or in separate (e.g., stacked) shapes with different concentrations of bio-sensing ink—in the composite 400. For example, the bacterial composite 400 may be printed in a pattern that contains increasing concentrations of the bacterial ink 430. The increasing concentrations of bacteria may correlate to an intensity scale for exposure or presences of particular stimuli.

In other aspects, graphics, symbols, or other indicia incorporated into one or more layer of the tattoo 10 may become visible or invisible in response to the internal or external stimuli. The internal or external stimuli may cause direct fluorescence, luminescence, chemiluminescence, a color change or a pulsing color/light on a transparent or opaque medium of the tattoo 10. A visual display may also be brought about by physical movement or motility change of the bacteria within the microfluidic channels 700, as shown in FIGS. 6 and 7 or another enclosed area with the tattoo 10. Visual displays may also be brought about by thermal changes within the composite 400 or electrical stimuli, which may be measured by or provided by an external device.

In one embodiment as shown in FIG. 7, various analytes 800 which may be internal or external stimuli transverse the substrate 500, as generally indicated by 810. The analytes 800 contact the bacteria 410 within the bacterial composite 400. In this embodiment, the bacteria 410 or a response induced by the analyte within the bacteria may travel along a pathway 710 to further generate a visual display 820 which may be observed, indicated by 830, by a user of the tattoo 10, another external observer, or a device (not shown). In other embodiments, the visual display 820 may be generated within the bacterial composite 400, where observers may observe a visual change in the bacterial composite 400, including but not limited to a color change or deformation of the composite.

Moreover, a visual display may be provided by physical deformation of the tattoo 10 itself. For example, a shape or structural change may be observed when the bacterial composite reacts to the analyte to increase or decrease pressure on the application site to produce a protruding shape/bump or a recessed shape or depression. In one aspect, the physical changes may be caused by a chemical reaction resulting in off gassing to inflate/deflate the encapsulation layer 300.

Each of the foregoing processes can be used to cause the display of an icon, text, a progress bar or any desired or arbitrary image, pattern, or graphic on the tattoo 10. etc. The visual display features of the bacterial tattoo 10 may enhance visual recognition when used as a sensor. Alternately, the visual display features may simply serve an aesthetic or ornamental purpose and enable greater design customization for the user regardless of the functionality of the sensor.

Example Uses and Devices that Incorporate the Bacterial Tattoo

Skin-Based Electronics

The bacterial tattoo 10 or devices that incorporate the tattoo may be used in a variety of forms as a wearable device that senses and conveys information about the devices internal and external environments. Various embodiments of the bacterial tattoo 10 may also be used to gather and convey information through a skin-based device that is extremely thin, flexible, compliant, and comfortable to the user's skin. These embodiments may be hidden under someone's clothing without adding, bulky volume or weight, or it could be shown as a fashion or graphic pattern and function more like as person's second skin rather than a bulky device or accessory.

In one example, the bacterial tattoo's may provide means for detecting and monitoring intoxication by measuring ethanol or other metabolites excreted through a wearer's skin. In another example, the bacterial tattoo 10 may be worn as a fashion accessory by those who want to be fashionable, dynamic and high-tech by displaying customizable and variable tattoos.

Medical Devices, Diagnostics & Sensors

The bacterial tattoo 10 may be used as an external medical diagnostic or sensing device. The bacterial composite 400 may be configured to sense a variety of internal/external stimuli relevant to a medical diagnosis, testing, or monitoring during therapeutic treatment steps to ensure patient safety. In these embodiments, the tattoo 10 is applied directly to the skin. In another example, the tattoo 10 may be worn for self-monitoring by people who want to monitor and learn more about their own physiological behavior and changes.

Using existing technology monitoring someone's temperature, for example, typically requires a traditional passive thermometer, electronic thermometer, infrared laser heat sensor or requires a patient to be plugged into an external device. In contrast, the tattoos if the present disclosure may be placed on the patient's skin which would continuously sense and visually represent the change in temperature, without external power, bulky components or complex devices. Various other testing and monitoring uses, including athletic testing and monitoring, may be utilized without straying from the spirit of the disclosure. In other examples, the bacterial tattoo 10 may be used in medical facility settings to monitor for infants or other patients who cannot communicate their physiological state. The tattoo 10 may also be used for pregnancy or fertility testing, as well as monitoring glucose/insulin levels for diabetics who need to monitor their glucose/insulin levels constantly.

Commercial Applications

The tattoo 10 may be used in a wide variety of commercial applications. In one example, the tattoo 10 may be used for sports and athletic monitoring. In particular, endurance athletes such as runners, cyclists, and swimmers may place the tattoo 10 on their skin during training and competition. Similarly, the tattoo 10 may be incorporated on to the clothing of athletes, miners, or others for monitoring external environmental conditions.

Figure 9:
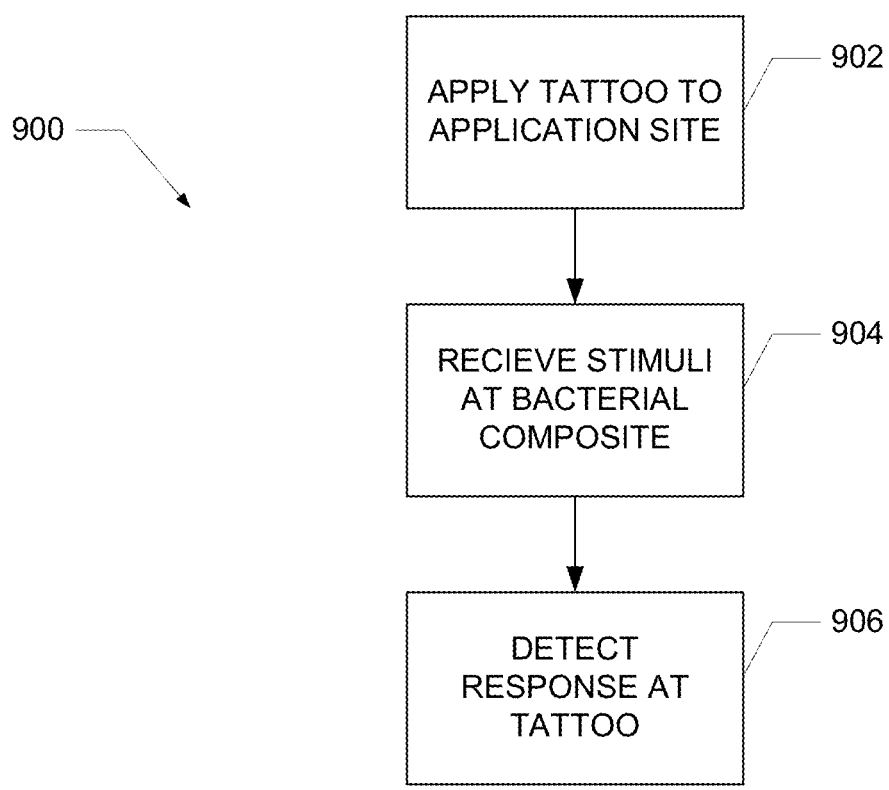
FIG. 9 is a flowchart depicting a method of using the programmable bacterial tattoo according to one embodiment.

In one embodiment, as shown in FIG. 9, a method 900 for use of the tattoo 10 includes applying the tattoo to an application site at step 902. At step 904, the bacterial composite 400 receives internal stimuli, external stimuli, or both. A response 820 generated by the bacteria is detected at 906. In other aspects, the method 900 may further include removing the backer 100 by dissolving the water soluble layer 200 during application of the tattoo 10. Additionally, the detection of the response may further include visual observing the tattoo 10, contacting the tattoo to perceive a tactile response, or contacting the tattoo 10 with an external device.

In various other aspects, the tattoo 10 may be used to provide smart signage on products, objects, structures, or even buildings. In this example, the tattoo 10 provides marketing and advertising companies or business owners with the ability to place a dynamic logo on a person, packaging, labels, and signs.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in to best explain the principles of the technology, its practical application, and to enable others skilled in the art to utilize the technology in various embodiments and with various modifications as are suited to the particular use contemplated. It is intended that the scope of the technology be defined by the claim.

What is claimed is:

1. A flexible programmable bacterial tattoo comprising:
a flexible adhesive substrate comprising one or more microfluidic channels configured in a predetermined pattern, wherein the flexible adhesive substrate is adhered to a surface;
a water-soluble layer;
a bacterial composite disposed between the water-soluble layer and the adhesive substrate and deposited within the microfluidic channels of the adhesive substrate;
a removable backer engaged to the water-soluble layer, wherein dissolution of the water-soluble layer removes the removable backer; and,
where, in response to an analyte, the bacterial composite within the microfluidic channels of the adhesive substrate exhibits altered motility and generates an optical output or a visual display in the programmable bacterial tattoo.

2. The bacterial tattoo of claim 1, further comprising an encapsulation layer engaged to the adhesive substrate opposite the bacterial composite, wherein the bacterial composite further comprises one or more bacterial strains encapsulated in a microcapsule distinct from the encapsulation layer.

3. The bacterial tattoo of claim 2, wherein the encapsulation layer further comprises a porous one-way membrane.

4. The bacterial tattoo of claim 1, wherein the adhesive substrate comprises a porous one-way membrane.

5. The bacterial tattoo of claim 2, wherein the microcapsule comprises at least one of agarose or alginate.

6. The bacterial tattoo of claim 1, wherein the bacterial composite further comprises one or more bacterial strains selected to respond to a particular analyte.

7. The bacterial tattoo of claim 1, wherein the bacterial composite further comprises one or more bacterial strains, and wherein the one or more bacterial strains are selected to respond to a presence of at least one of a sugar ethanol, ultraviolet radiation, infrared radiation, ionizing radiation, a change in temperature, and other microorganisms.

8. The bacterial tattoo of claim 1, wherein the bacterial composite further comprises one or more genetically modified bacterial strains.

9. The bacterial tattoo of claim 1, wherein the optical output occurs within the microfluidic channels of the adhesive substrate, the optical output corresponding to the pattern.

10. The bacterial tattoo of claim 9, wherein the optical output comprises at least one of fluorescence, colorimetric changes, luminescence, or chemiluminescence.

11. The bacterial tattoo of claim 1, wherein the bacterial composite further generates an electrical output in response to an analyte.

12. The bacterial tattoo of claim 11, wherein the electrical output comprises at least one of changes in pH of the bacterial composite or changes in conductivity through the bacterial composite.

13. The bacterial tattoo of claim 1, wherein altered motility comprises tumbling, swimming, or spreading behavior of bacteria within the bacterial composite.

14. The bacterial tattoo of claim 1, wherein the visual display is distinct from the pattern.

15. The bacterial tattoo of claim 14, wherein the visual display comprises the display of an arbitrary image, arbitrary text, arbitrary graphic, or other arbitrary indicia.

16. A flexible programmable bacterial tattoo comprising:
a flexible adhesive substrate comprising one or more microfluidic channels configured in a predetermined pattern, wherein the flexible adhesive substrate is adhered to a surface, and wherein the predetermined pattern presents a logic-based pathway wherein sequential reactions within the programmable bacterial tattoo are governed by "if-then" conditions;
a water-soluble layer;
a bacterial composite disposed between the water-soluble layer and the adhesive substrate and deposited within the microfluidic channels of the adhesive substrate;
a removable backer engaged to the water-soluble layer, wherein dissolution of the water-soluble layer removes the removable backer; and,
where, in response to an analyte, the bacterial composite within the microfluidic channels of the adhesive substrate generates an optical output or a visual display in the programmable bacterial tattoo.

17. The bacterial tattoo of claim 16, wherein the adhesive substrate comprises a porous one-way membrane.

18. The bacterial tattoo of claim 16, further comprising an encapsulation layer.

19. The bacterial tattoo of claim 16, further comprising where the bacterial composite generates an electrical output in response to an analyte.

20. The bacterial tattoo of claim 19, where the electrical output comprises at least one of changes in pH of the bacterial composite or changes in conductivity through the bacterial composite.

* * * * *